United States Patent
Fernández Gutiérrez et al.

(10) Patent No.: US 10,226,327 B2
(45) Date of Patent: Mar. 12, 2019

(54) REFRACTIVE MULTIFOCAL INTRAOCULAR LENS WITH OPTIMISED OPTICAL QUALITY IN A RANGE OF FOCUS AND METHOD TO PRODUCE IT

(71) Applicant: CONSEJO SUPERIOR DE INVESTIGACIONES CIENTÍFICAS (CSIC), Madrid (ES)

(72) Inventors: David Fernández Gutiérrez, Madrid (ES); Sergio Barbero Briones, Madrid (ES); Carlos Dorronsoro Díaz, Madrid (ES); Susana Marcos Celestino, Madrid (ES)

(73) Assignee: CONSEJO SUPERIOR DE INVESTIGACIONES CIENTÍFICAS (CSIC), Madrid (ES)

( * ) Notice: Subject to any disclaimer, the term of this patent is extended or adjusted under 35 U.S.C. 154(b) by 0 days.

(21) Appl. No.: 14/655,085

(22) PCT Filed: Dec. 27, 2013

(86) PCT No.: PCT/EP2013/078087
§ 371 (c)(1),
(2) Date: Jun. 24, 2015

(87) PCT Pub. No.: WO2014/102352
PCT Pub. Date: Jul. 3, 2014

(65) Prior Publication Data
US 2015/0342727 A1 Dec. 3, 2015

(30) Foreign Application Priority Data
Dec. 27, 2012 (ES) .................................. 201232043

(51) Int. Cl.
*A61F 2/16* (2006.01)
*G05B 19/4097* (2006.01)
*G06F 17/10* (2006.01)

(52) U.S. Cl.
CPC ............ *A61F 2/1618* (2013.01); *A61F 2/164* (2015.04); *G05B 19/4097* (2013.01);
(Continued)

(58) Field of Classification Search
CPC .................... A61F 2/1618; A61F 2/164; A61F 2250/0036; A61F 2250/0053; A61F 2250/0091
See application file for complete search history.

(56) References Cited

U.S. PATENT DOCUMENTS 4,537,479 A * 8/1985 Shinohara .............. G02C 7/024
351/159.42
4,580,882 A * 4/1986 Nuchman ............ G02B 5/1876
351/159.41
(Continued)

FOREIGN PATENT DOCUMENTS

DE 10 2007 057 122 A1 6/2008
DE 102007057122 A1 6/2008
(Continued)

OTHER PUBLICATIONS

"Aphakic Eye," The Free Dictionary, <http://medical-dictionary.thefreedictionary.com/aphakic+eye> [retrieved Feb. 3, 2017], 15 pages.
(Continued)

*Primary Examiner* — Paul B Prebilic
(74) *Attorney, Agent, or Firm* — Christensen O'Connor Johnson Kindness PLLC

(57) ABSTRACT

The present invention describes a refractive multifocal intraocular lens with aspheric geometry on both surfaces in such a way that the map of local optical strength of the lens, combined with the cornea, has a central region of intermediate optical strength surrounded by a ring of maximum optical strength, with a smooth transition between the two, after which it alternates smoothly between rings of varying strengths.

18 Claims, 2 Drawing Sheets

(52) U.S. Cl.
CPC ...... *G06F 17/10* (2013.01); *A61F 2002/1681* (2013.01); *A61F 2230/0063* (2013.01); *G05B 2219/35261* (2013.01)

(56) References Cited

U.S. PATENT DOCUMENTS

| | | | | |
|---|---|---|---|---|
| 5,112,351 | A * | 5/1992 | Christie | A61F 2/1618 351/159.08 |
| 5,225,858 | A * | 7/1993 | Portney | A61F 2/1618 351/159.42 |
| 5,326,348 | A * | 7/1994 | Nordan | A61F 2/164 623/6.24 |
| 5,691,797 | A * | 11/1997 | Seidner | G02C 7/042 351/159.47 |
| 5,715,031 | A * | 2/1998 | Roffman | G02C 7/028 351/159.44 |
| 5,805,260 | A * | 9/1998 | Roffman | G02C 7/042 351/159.21 |
| 6,210,005 | B1 * | 4/2001 | Portney | A61F 2/14 351/159.43 |
| 8,235,525 | B2 * | 8/2012 | Lesage | A61F 2/1613 351/159.74 |
| 2004/0034413 | A1 * | 2/2004 | Christensen | A61F 2/147 623/5.11 |
| 2005/0246016 | A1 * | 11/2005 | Miller | A61F 2/14 351/159.01 |
| 2007/0030444 | A1 * | 2/2007 | Chauveau | A61F 2/1618 351/159.42 |
| 2007/0168027 | A1 * | 7/2007 | Brady | A61F 2/1613 623/6.31 |
| 2010/0016965 | A1 | 1/2010 | Hong et al. | |
| 2010/0100178 | A1 * | 4/2010 | Weeber | A61F 2/1618 623/6.28 |
| 2011/0292335 | A1 * | 12/2011 | Schwiegerling | A61F 2/1613 351/159.44 |
| 2017/0216020 | A1 * | 8/2017 | Weeber | A61F 2/1618 |

FOREIGN PATENT DOCUMENTS

| | | |
|---|---|---|
| EP | 2 145 603 A1 | 1/2010 |
| EP | 2 591 753 A1 | 5/2013 |
| ES | 2 374 916 B1 | 2/2012 |
| WO | 88/09950 A1 | 12/1988 |
| WO | 01/18592 A1 | 3/2001 |
| WO | 2012/004746 A2 | 1/2012 |

OTHER PUBLICATIONS

Belin, M.W., et al., "Keratoconus/Ectasia Detection With a Modified (Enhanced) Reference Surface," in "Elevation Based Corneal Tomography," Chap. 8, JP Medical Ltd., May 18, 2012, pp. 100-101.

International Preliminary Report on Patentability dated Jun. 30, 2015, and Written Opinion of the International Searching Authority dated Mar. 18, 2014, issued in corresponding International Application No. PCT/EP2013/078087, filed Dec. 27, 2013, 7 pages.

Lin, J.T., and A. Garg, "Comparing Methods of IOL Power Calculations," in "Mastering the Presbyopic Surgery Lenses & Phakic IOLs," Chap. 5, Jaypee Brothers Ltd., New Delhi, Jun. 2007, pp. 44-65.

"Mathematical Optimization," Wikipedia, The Free Encyclopedia, Jan. 27, 2017, <https://en.wikipedia.org/wiki/Mathematical_optimization> [retrieved Feb. 3, 2017], 11 pages.

"Optical Axis," Britannica Online Encyclopedia, <https://www.britannica.com/technology/print/article/430358> [retrieved Feb. 3, 2017], 1 page.

"Polar Coordinate System," Wikipedia, The Free Encyclopedia, Oct. 13, 2016, <https://en.wikipedia.org/wiki/Polar_coordinate_system> [retrieved Feb. 3, 2017], 13 pages.

"Pseudophakia," The Free Dictionary, <http://medical-dictionary.thefreedictionary.com/pseudophakia> [retrieved Feb. 3, 2017], 2 pages.

International Search Report dated Mar. 18, 2014, issued in corresponding International Application No. PCT/EP2013/078087, filed Dec. 27, 2013, 4 pages.

"Strabismus," in S. Agarwal et al. (eds.), "Textbook of Ophthalmology," vol. 1, Section D, Jaypee Brothers, New Delhi, 2002, p. 422.

Taravella, M.J., and R.S. Davidson, "Corneal Topography and Wavefront Imaging," in Yanoff and Duker (eds.), Chap. 4.2, "Ophthalmology," 3rd ed., Elsevier Health Sciences, 2009, p. 209.

\* cited by examiner

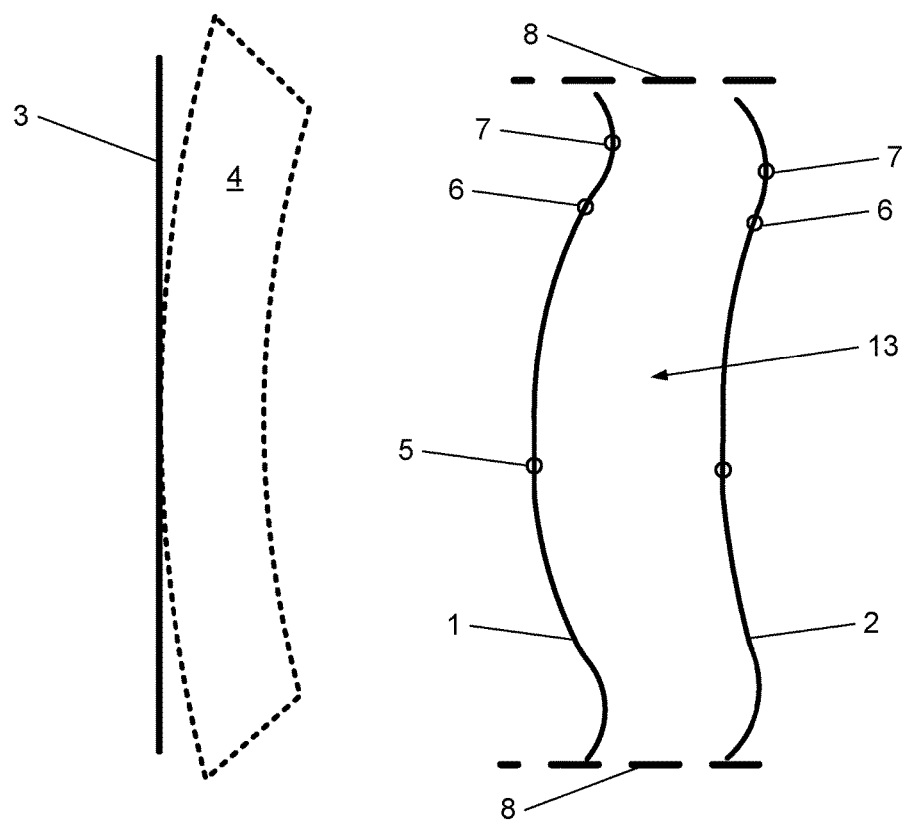
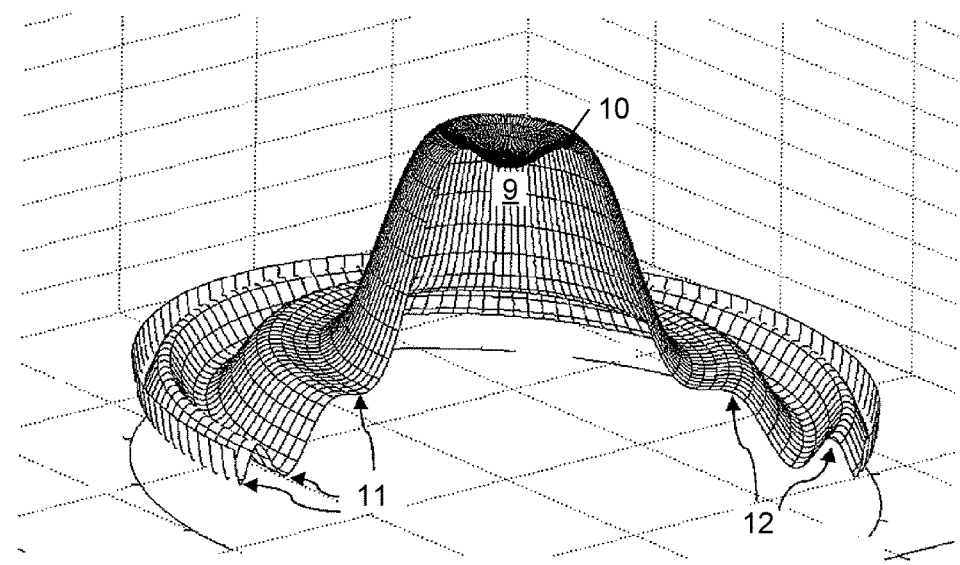

REFRACTIVE MULTIFOCAL INTRAOCULAR LENS WITH OPTIMISED OPTICAL QUALITY IN A RANGE OF FOCUS AND METHOD TO PRODUCE IT

TECHNICAL FIELD

The present invention relates, in general, to the field of ophthalmology, in particular to the design of ophthalmological lenses.

PRIOR ART

The human eye consists of two lenses, the cornea and the lens, which project images of the outside world onto the retina. The lens in the young eye is capable of modifying its shape and focusing objects which are close and far away, a process known as accommodation. The capability of accommodation is lost progressively with age. Furthermore, the lens loses transparency with age, a process known as the formation of cataracts. In cataract surgery, the natural lens of the eye is replaced by an intraocular lens.

The monofocal intraocular lenses return transparency to the eye. Furthermore, by knowing the ocular biometry of the patient, the strength of the intraocular lens is selected such that it corrects the refractive error of the patient.

The main parameters that are usually used to describe the design of the optics of an intraocular lens are the diameter of the optic region, the shape of the surfaces, the material used and the central thickness. The thickness at the edge of the lens is a derived quantity, as it can be obtained from the central thickness and from the shape of the surfaces, but it is of great importance as it represents the thickness of the region of connection to the haptics, which give mechanical stability to the lens inside the eye. The present invention relates solely to the optical design of an intraocular lens, which can be combined with different mechanical designs outside the optic region and in particular outside the haptics.

Recently, optical designs of monofocal, intraocular lenses which correct the spherical aberration of the cornea, or which, in general, try to optimise the optical quality of the distance vision in the fovea, or even in the peripheral regions of the field of vision, have been optimised. By implanting monofocal intraocular lenses as a substitute for the natural lens, the eye loses the ability of residual accommodation which it might have if the lens were to remain. If the strength of the lens is well adjusted to far distances, as is usually the norm, the patients cannot not see clearly up close with these lenses, needing an additional correction (generally glasses with positive refraction) to carry out near-vision tasks.

Previously, lenses with multiple focuses have been proposed, produced by means of principles of refractive optics and diffractive optics, to try to compensate for this problem. The refractive multifocal lenses proposed usually consist of an optic region divided into different sections. Normally, they have a circular central section and one or various peripheral annular regions, each one having different radii of curvature, in such a way that they achieve different strengths in the different sections of the optic region. For example, lenses with a circular central section of greater strength for near-distance, surrounded by a single ring of lesser strength for far-distance (U.S. Pat. No. 3,420,006), lenses with concentric sections with alternate rings for near and far-distance (U.S. Pat. No. 5,158,572, U.S. Pat. No. 6,835,204, U.S. Pat. No. 568,223) have been proposed. Lenses that use concentric sections with smooth transitions between them and aspheric regions or aspheric and spherical regions (U.S. Pat. No. 5,112,351, U.S. Pat. No. 5,326,348, U.S. Pat. No. 5,715,031) have also been used. Recently, segments have been proposed that are not concentric with a section for far-distance and another for near-distance (US20120029631, U.S. Pat. No. 7,287,852). Lenses with aspheric outlines, with a continuously variable refractive outline which allows an increase in the depth of focus (U.S. Pat. No. 4,580,882) have also been proposed.

Multi-region outlines (U.S. Pat. No. 7,381,221) and aspheric outlines (i.e. Tecnis or Acrysof) for the purpose of focusing light into one single focus, combining the optics of the cornea with that of the intraocular lens, and correcting the higher-order aberrations of the eye, have also been used. In particular, aspheric designs with coefficients of up to the order of 10 (U.S. Pat. No. 4,504,982) have been proposed for this purpose.

As well as the refractive multifocal lenses, diffractive lenses are an alternative solution. These lenses work by means of principles of diffractive optics and focus the light into two focuses, one at far-distance and the other at near-distance (US20090088840). Trifocal designs (US20110292335, EP20110181646, US20120224138, U.S. Pat. No. 8,235,525) with an intermediate focus have also been proposed.

Multi-region refractive lenses can present problems of diffraction (halos due to abrupt changes of strength between regions), present performance limitations due to the size of the pupil of the patient being variable, and in general are limited to two or three focuses, providing blurred images at intermediate focal positions. Even though they achieve a certain increase in the depth of focus, the proposed aspheric designs allow little control of the optical quality by means of the focus.

One of the disadvantages of the diffractive lenses is the quality of the image in the intermediate focal regions; outside the peaks corresponding to the focuses of the design, said quality is very low due to the images being out of focus. Another of the disadvantages of the diffractive lenses is that they are optimised for a given wave length and cause colour effects such as halos in polychromatic light. The diffractive lenses, however, present multifocal properties (simultaneous vision) for any diameter of the pupil of the eye, the multifocal performance thereof not being limited by the lighting conditions and the effect of pupillary miosis.

DESCRIPTION OF THE INVENTION

Brief Description

An object of the invention is a refractive multifocal intraocular lens, used to replace the lens of the eye, hereinafter the lens according to the invention, wherein:
a) in its optic region, said lens comprises a front optical surface and a back optical surface, both being aspheric and cut from a predetermined transparent material, said front optical surface and back optical surface further being separated by a predetermined central thickness,
b) an elevation map of each of said front optical surface and back optical surface has rotational symmetry with respect to the optical axis of said lens and a progressive and continuous evolution along the entire topography,
c) an elevation along the radial coordinate on both said front optical surface and back optical surface, taking the tangential plane to the corneal apex as a reference, has a local minimum of zero, which corresponds to the centre of said lens, said elevation further presenting one or more turning points of curvature before reaching at least one peripheral local maximum, situated inside said optic region and at a predetermined distance from the edge of said optic region, giving rise to a topography that presents a local elevation minimum in the centre and at least one ring inside said optic region that presents a local elevation maximum, and d) a map of local optical strength inside said optic region, resulting from the combined optical refraction of said two aspheric optical surfaces and a model cornea, which is external and to the front of said lens, has rotational symmetry around the optical axis, and a central region of intermediate optical strength, surrounded by a ring of maximum optical strength with a progressive transition between them, after which rings of varying strength alternate progressively and in particular at least one ring, the optical strength of which represents a local minimum, with at least one ring, the optical strength of this represents a local maximum.

Another object of the invention is a method to produce the lens according to the invention, hereinafter the method according to the invention, which comprises at least the following steps:

a) mathematical definition of an aphakic eye model, described at least by the geometry of the surface or surfaces that define the cornea, the axial position of the retina and the axial position of the plane where the intraocular lens will be situated after an implantation, b) mathematical definition of a pseudophakic eye model, described by an aphakic eye model in which a model of a defined lens is implanted by means of a combination of variable descriptive parameters within a combination of boundary conditions which determine the geometry and the characteristics of said lens, c) definition of a merit function multiconfiguration which describes the optical quality of said pseudophakic eye model, said function integrating multiple configurations, each one corresponding to a distance to the objective plane, associating a weight to each of said configurations to produce, as a result, a single value that represents the quality of the image of the evaluated system at different distances to the objective plane, and d) optimisation of said combination of descriptive parameters which define said model lens to determine a combination of descriptive parameters which produces the optimal result of said merit function multiconfiguration.

Another object of the invention is a refractive multifocal intraocular lens which is produced by the method according to the invention.

DETAILED DESCRIPTION

The present invention describes, for the first time, a refractive multifocal intraocular lens with aspheric geometry on both surfaces in such a way that the map of local optical strength of the lens, combined with the cornea, has a central region of intermediate optical strength, surrounded by a ring of maximum optical strength with a smooth transition between them, after which rings of varying strength alternate smoothly.

The lens provides a stable performance in terms of image quality, both by means of the focus and by means of changes to the pupil, and provides the patient with high-contrast vision simultaneously and with an optical quality which has been optimised for objects situated at a wide range of distances, from far away to up close, passing through the intermediate distances without relevant decreases in the quality along the focus, in contrast to the previous refractive and diffractive designs (FIG. 3). The lens, which is the object of this invention, has aspheric geometry in both surfaces which allows concentric regions of different strengths to be produced, but with smooth transitions between them, and has been designed in a way which optimises the optical quality for various distances simultaneously, with a geometry and a map of strengths which are very different to those of the refractive multifocal intraocular lenses which form part of the prior art.

Furthermore, the global optimisation of the design provides the highest possible quality for the combination of all of the regions, combined with the optical quality of the cornea of the model of the pseudophakic eye on which the design is developed, in a very different way from simple multi-region solutions of different curvature over the different regions of the lens. Furthermore, the resulting map of variable strengths of the lens bestows similar multifocal performances over a wide range of pupils of different sizes (FIG. 4).

Furthermore, a method is described to produce it, by means of the optimisation of its design parameters, using a merit function of multiconfiguration which simultaneously integrates multiple configurations each one corresponding to a different distance to the objective plane. The present invention thus achieves a multifocal design with an optimised optical quality by means of the focus and thus is superior to other solutions that have not been optimised.

The lens according to the invention overcomes many of the disadvantages described in previous refractive and diffractive multifocal designs. In particular, the lens according to the invention provides high-quality optics in intermediate sections, in contrast to the multi-region refractive and conventional diffractive multifocal designs, which provide a blurred image in many regions of intermediate vision. Additionally, the lens according to the invention provides an optical quality with few variations in a wide range of pupils, its performance thus being independent of the size of the natural pupil of the subject, of changes in ambient lighting or of changes in the diameter of the pupil associated with accommodative effort. In this sense, the lens according to the invention overcomes the limitations described in previous multifocal intraocular lenses.

The optimisation of the optical quality, which is carried out in combination with a model cornea and simultaneously in a wide section of focus, is one of the most relevant characteristics of this invention. The present invention provides a method to design a multifocal intraocular lens with optimised optical quality by means of the focus, preferably for objects situated between infinity and 0.4 m, characterised by an aspheric surface geometry which provides an elevation map of each of the surfaces which has rotational symmetry with respect to the optical axis of the lens, and a smooth evolution along the entire topography.

As well as providing the lens, which is the object of the invention, with an optimised and stable optical quality in a wide range of focal positions, the smooth alternation between local maximums and minimums on the map of optical strengths, which is emphasised at the periphery, equips this lens with a stable performance with respect to different pupillary diameters. Both characteristics mean that the performance of the lens exceeds the prior art.

Thus, an object of the invention is a refractive multifocal intraocular lens, used to replace the lens of the eye, hereinafter the lens according to the invention, wherein:

a) in its optic region, said lens comprises a front optical surface and a back optical surface, both being aspheric and cut from a predetermined transparent material, said front optical surface and back optical surface further being separated by a predetermined central thickness, b) an elevation map of each of said front optical surface and back optical surface has rotational symmetry with respect to the optical axis of said lens and a progressive and continuous evolution along the entire topography, c) an elevation along the radial coordinate on both said front optical surface and back optical surface, taking the tangential plane to the corneal apex as a reference, has a local minimum of zero, which corresponds to the centre of said lens, said elevation further presenting one or more turning points of curvature before reaching at least one peripheral local maximum, situated inside said optic region and at a predetermined distance from the edge of said optic region, giving rise to a topography that presents a local elevation minimum in the centre and at least one ring inside said optic region that presents a local elevation maximum, and d) a map of local optical strength inside said optic region, resulting from the combined optical refraction of said two aspheric optical surfaces and a model cornea, which is external and to the front of said lens, has rotational symmetry around the optical axis, and a central region of intermediate optical strength, surrounded by a ring of maximum optical strength with a progressive transition between them, after which rings of varying strength alternate progressively and in particular at least one ring, the optical strength of which represents a local minimum, with at least one ring, the optical strength of this represents a local maximum.

A particular object of the invention is the lens according to the invention, wherein the optic region has a diameter between 4 and 7 mm.

Another particular object of the invention is the lens according to the invention, wherein the lens has an optimised optical quality by means of the stable focus where the diameter of the pupils is in a range between 5 and 2.5 mm.

Another particular object of the invention is the lens according to the invention, wherein strength of the lens for distance vision is between +5 and +40 D.

Another particular object of the invention is the lens according to the invention, wherein the lens has a central thickness between 0.5 and 2 mm.

Another particular object of the invention is the lens according to the invention, wherein the lens has a continuous transition region from the optical zone to the haptic.

Another particular object of the invention is the lens according to the invention, wherein the lens has:

a) an optical strength for distance vision of a value of 22 D,
b) a refractive index of the material of a value of n=1.5387,
c) a front surface that is defined by means of the following parameters: r=7.365103 mm; k=10.737215, $a_2$=0.09119, $a_3$=−0.030423, $a_4$=4.160235e$^{-3}$, $a_5$=−5.237021e$^{-4}$,
d) a back surface which is defined by means of the following parameters: R=−0.262811 mm; K=−3.690784e$^{+39}$, $a_2$=0.128675, $a_3$=−0.046277, $a_4$=4.546855e$^{-3}$, $a_5$=−1.458619e$^{-4}$,
e) a central thickness of a value of $e_c$=1.216464 mm, and
f) an optimised and uniform optical quality for objects at a distance of between infinity and 0.4 m.

Another object of the invention is a method of producing the lens according to the invention, hereinafter the method according to the invention, which consists of at least the following steps:

a) mathematical definition of an aphakic eye model, described at least by the geometry of the surface or surfaces that define the cornea, the axial position of the retina and the axial position of the plane where the intraocular lens will be situated after an implantation, b) mathematical definition of a pseudophakic eye model, described by an aphakic eye model in which a model of a defined lens is implanted by means of a combination of variable descriptive parameters within a combination of boundary conditions which determine the geometry and the characteristics of said lens, c) definition of a merit function multiconfiguration which describes the optical quality of said pseudophakic eye model, said function integrating multiple configurations, each one corresponding to a distance to the objective plane, associating a weight to each of said configurations to produce, as a result, a single value that represents the quality of the image of the evaluated system at different distances to the objective plane, and d) optimisation of said combination of descriptive parameters which define said model lens to determine a combination of descriptive parameters which produces the optimal result of said merit function multiconfiguration.

In step a) the geometry of the surface or surfaces that define the cornea (see number 4 on FIG. 1) are generally described by means of aspheric mathematical surfaces. The geometric description of the aphakic eye does not necessarily need to be complete; it can be partial. Optical defects (be it those determined by a determined topography of the cornea or by an object of the ideal phase) can be added to the description in simple geometric terms, said defects generally referring to optical aberrations, and in particular to those that are low-order, such as myopia, hyperopia and astigmatism. In a particular embodiment of the invention, said geometric parameters correspond to descriptive parameters, which are representative of a population, which can be as general as is desired, or descriptive of a particular group of the population (be it defined by age, ethnicity, refractive error or of patients who have previously had corneal surgery, among others). In another particular embodiment of the invention, they can be parameters which are measured individually for each patient by biometric techniques.

A particular object of the invention is the method according to the invention in which the front and back surfaces (see numbers 1 and 2 on FIG. 1) of the model lens of step b) are aspheric, have an elevation map with rotational symmetry with respect to the optical axis of the lens and a smooth and continuous evolution along the entire topography. In a preferred embodiment of the method according to the invention, but not limited according to the invention, the model lens of stage b) consists of two aspheric surfaces, one front (see number 1 on FIG. 1) and the other back (see number 2 on FIG. 1), defined by the radius of curvature, conicity and constants of asphericity according to the following equation:

$$z = \frac{c*r^2}{1+\sqrt{1-(1+k)*c^2*r^2}} + \sum a_i * r^{2i}$$

wherein:
z=plane parallel to the surface at a determined radius "r" from the centre,
c=curvature in the centre,
k=constant of conicity, and
$a_i$=each one of the coefficients of asphericity of the order 4, 6, 8, 10 and so on.

Another preferred embodiment of the invention is the method according to the invention in which the distances to the object plane of step c), in which the optical quality is optimised simultaneously, are distances that are preferably from infinity to 0.2 m. The integration of the different configurations into the merit function multiconfiguration can be found by multiplying the result of each one of the configurations by certain weights which determine the relative importance of the vision at different distances and ensure the convergence of the subsequent optimisation. The result of the merit function multiconfiguration provides an estimate of optical quality, according to the parameters of the model lens.

Another preferred embodiment of the invention is the method according to the invention in which the result of the merit function multiconfiguration is produced by tracing rays across the pseudophakic eye (which includes the model lens), for each one of the configurations (corresponding to each objective distance). The numerical evaluation of the optical quality in each configuration can be embodied in different ways, well known in the field of optical design, such as, for example, in terms of the mean square root of the wave front in the plane of the pupil or of the diagram of impact in the plane of the image.

Another preferred embodiment of the invention is the method according to the invention in which step d) of the optimisation is carried out by an iterative process.

The method according to the invention is carried out similarly for eyes with different axial length, and therefore is capable of receiving intraocular lenses of a different strength for distance vision.

Another particular object of the invention is the method of the invention wherein the lens is a refractive multifocal intraocular lens of a determined strength for distance vision and wherein, in the definition of the aphakic eye model, the axial length is used such that a focused retinal image is produced with a spherical monofocal lens of equal refractive strength. More concretely, in a preferred embodiment, the nominal strength for distance vision of the refractive multifocal lens is allocated to that, the design of which is optimised in a range of focus for an eye with an axial length such that a monofocal lens with spherical surfaces, the same material and the same thickness, and with this same nominal strength, will produce the better image of an object situated at 5 meters above the retina.

Finally, another object of the invention is a refractive multifocal intraocular lens which is produced by the process according to the invention.

DESCRIPTION OF THE FIGURES

FIG. 1.—Geometry of the cornea of the eye according to design and to the lens of the invention. Front optical surface 1 of the lens, back optical surface 2 of the lens, tangent plane 3 at the apex of the cornea 4, local minimum of zero 5 which corresponds to the centre of the lens, and one or more turning points of curvature 6, peripheral local maximum 7 and edge of the optic region 8.

FIG. 2.—Map of strengths produced from the combination of the refraction of the rays of light on the two aspheric optical surfaces of the lens according to the invention and a model cornea, which is external and to the front of the lens 13. Central region of intermediate optical strength 9, ring of maximum optical strength 10, a ring, the optical strength of which is a local minimum 11 with at least one ring, the optical strength of which is a local maximum 12.

EXEMPLARY EMBODIMENT OF THE INVENTION

Figure 3:
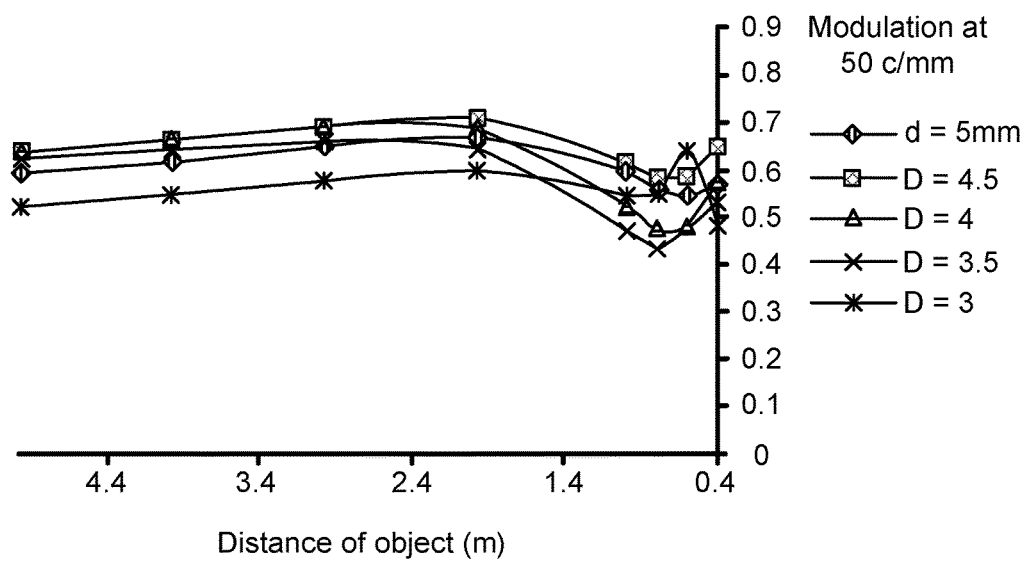
FIG. 3.—Modulation transfer function of the eye according to design with the lens according to the invention for a spatial frequency of 50 c/mm according to the objective distance, for different diameters of the pupil. The different lines and symbols represent the performance for different diameters of the pupil (D) between 5 and 3 mm.

By way of illustrating the present invention, an exemplary embodiment of a refractive multifocal lens with a diameter of the pupil of 5 mm (effective diameter of the optical area of the lens of 4.3 mm) and a refractive index of 1.5387 (hydrophobic material) is described.

To produce the design of the proposed lens, a model of an eye with the following geometrical parameters is used, collected in Table 1:

TABLE 1

| Surface | Radius (mm) | Conicity | Thickness (mm) | Index |
| --- | --- | --- | --- | --- |
| Tear film | 7.79 | −0.015 | 0.004 | 1.337 |
| Epithelium | 7.79 | −0.015 | 0.054 | 1.376 |
| Stroma | 7.556 | −1.43 | 0.473 | 1.376 |
| Aqueous | 6.53 | −0.455 | 4.11 | 1.337 |
| Vitreous | — | — | Variable | 1.337 |

Table 2 shows the values produces for the geometric parameters of the multifocal refractive lens in the preferred embodiment of the invention (two aspheric surfaces, each with 7 parameters), $e_c$ being the central thickness of the lens.

TABLE 2

| Sur | C | $e_c$ | K | $a_1$ | $a_2$ | $a_3$ | $a_4$ | $a_5$ |
| --- | --- | --- | --- | --- | --- | --- | --- | --- |
| 1 | 0.135775 | 1.216464 | 10.737215 | 0 | 0.091190 | −0.030423 | −0.004160 | −0.000523 |
| 2 | −3.804871 | | −3.6908E+39 | 0 | 0.128675 | −0.046277 | −0.004547 | −0.000145 |

The outline of the front and back surfaces of the designed refractive intraocular lens is shown graphically in FIG. 1. As can be seen in FIG. 1, on both the front optical surface 1 of the lens and the back 2, the elevation along the radial coordinate, taking the tangent plane 3 at the apex of the cornea 4 as a reference, has a local minimum of zero 5, which corresponds to the centre of the lens and one or more turning points of curvature 6 before reaching at least one peripheral local maximum 7, situated inside the optical zone and at a certain distance from the edge of the optic region 8, giving rise to a topography which contains a local elevation minimum in the centre and at least one ring inside the optic region which is a local elevation maximum.

FIG. 2 depicts the map of strengths obtained from the combination of the aphakic eye model of the refraction of the rays of light on the two aspheric optical surfaces of the lens, the front 1 and the back 2, and a model cornea, which is external and to the front of the lens 13. Said map of strengths additionally characterises the objective lens of this invention and shows the alternations of annular regions of different refractive strength with a smooth transition between them. Within the optic region, the local optical strength has rotational symmetry around the optical axis, and a central region of intermediate optical strength 9 surrounded by a ring of maximum optical strength 10 with a smooth transition between them, after which rings of varying strength alternate smoothly and in particular at least one ring, the optical strength of which is a local minimum 11, with at least one ring, the optical strength of which is a local maximum 12.

In this embodiment of the invention, the merit function multiconfiguration is formed by adding the mean square root of the wave front of each configuration corresponding to the observation distances, which are 5; 4; 3; 2; 1; 0.8; 0.6 and 0.4, with the normalised weights 0.311; 0.044; 0.044; 0.044; 1.78; 0.088; 0.088; 0.444 respectively. A central thickness of between 0.6 and 1.2 mm; a peripheral thickness of between 0.25 and 0.4 mm haptics and maximum parallel plane of 1.5 mm have been considered as boundary conditions.

In order to evaluate the performance of the new refractive multifocal intraocular lens, this has been evaluated by a computer with regard to the generic eye of the design by means of conventional ray-tracing algorithms (Zemax). The performances of the new lens are described by means of the modulation transfer function (MTF) at 50 c/mm of the pseudophakic eye model, implanted with said lens across the focus. In FIG. 3, the evolution of the modulation for different objective distances is shown, according to the diameter of the pupil. The MTF remains at values greater than 0.45 in the entire range of focus (pupil diameter between 3 and 5 mm), reaching 0.65 for near and far distances and 0.58 for intermediate distances (for a pupil diameter of 4.5 mm). These values are similar to or greater than those obtained in the focuses of the distance or near vision of a diffractive multifocal lens of the prior art on the market, but the refractive multifocal intraocular lens, which is object of the invention, produces much greater values in the intermediate zone, which thus describe a good optical quality for intermediate vision.

Figure 4:
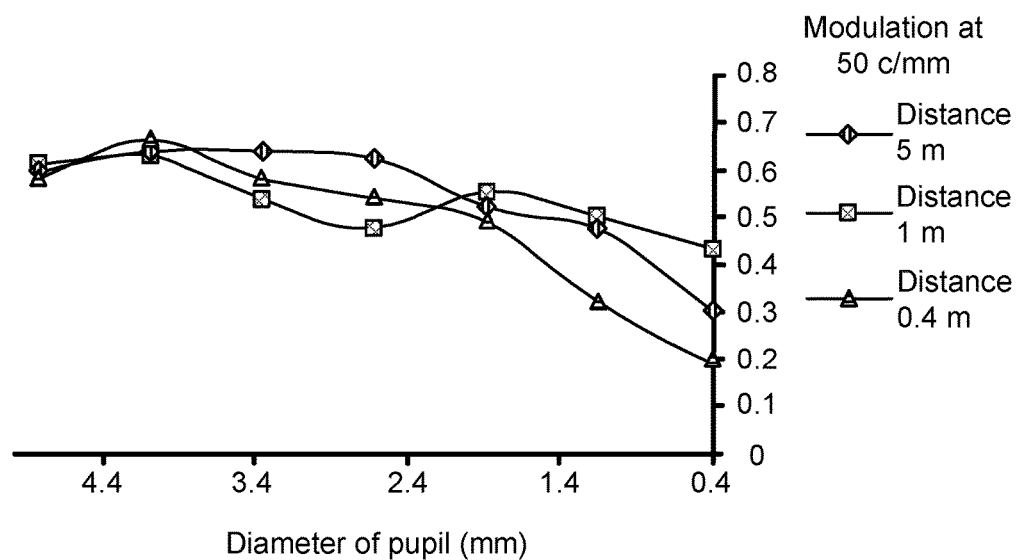
FIG. 4.—Modulation transfer function of the eye according to the design with the lens according to the invention for a spatial frequency of 50 c/mm according to the papillary diameter, for different objective distances. The different lines and symbols represent the performance for different objective distances, between 0.4 and 5 m.

The optical quality of this lens according to the size of the pupil remains practically constant between 3 and 5 mm diameter of the pupil, as is shown in FIG. 4.

The lens grants multifocal performances of similar characteristics to those already described, combined with different model eyes based on biometric data different to that of the eye according to design, corresponding to real eyes.

The invention claimed is:

1. Refractive multifocal intraocular lens, used to replace a lens of an eye, comprising:
    a front optical surface and a back optical surface in an optic region of said lens, both surfaces being aspheric and cut from a predetermined transparent material, said front optical surface and back optical surface further being separated by a predetermined central thickness,
    wherein an elevation map of each of said front optical surface and back optical surface has rotational symmetry with respect to an optical axis of said lens and a progressive and continuous evolution along an entire topography,
    wherein an elevation along a radial coordinate on both said front optical surface and back optical surface, taking a tangential plane to a corneal apex as a reference, has a local minimum of zero, which corresponds to a centre of said lens, and from said centre the elevation in the radial coordinate on both said front and back optical surfaces includes at least one turning point where curvature changes from concave to convex or from convex to concave before reaching at least one peripheral local maximum, situated inside said optic region and at a predetermined distance from an edge of said optic region, giving rise to a topography that presents a local elevation minimum in the centre and at least one ring inside said optic region that presents a local elevation maximum, and
    wherein a map of local optical strength inside said optic region, resulting from a combined optical refraction of said two aspheric optical surfaces and a model cornea, which is external and to the front of said lens, has rotational symmetry around the optical axis, and a central region of intermediate optical strength, surrounded by a ring of maximum optical strength with a progressive transition between them, after which rings of varying strength alternate progressively and in particular at least one ring, the optical strength of which represents a local minimum, with at least one ring, the optical strength of which represents a local maximum.

2. Refractive multifocal intraocular lens according to claim 1, wherein said optic region has a diameter between 4 and 7 mm.

3. Refractive multifocal intraocular lens according to claim 1, where a stable and optimised focus in a range of diameter of the pupil between 5 and 2.5 mm is provided.

4. Refractive multifocal intraocular lens according to claim 1, comprising a strength for distance vision between +5 and +40 D.

5. Refractive multifocal intraocular lens according to claim 1, comprising a central thickness between 0.5 and 2 mm.

6. Refractive multifocal intraocular lens according to claim 1, comprising a continuous transition region from the optical region to an haptic.

7. Method to manufacture a refractive multifocal intraocular lens according to claim 1, comprising at least the following steps: a) model an aphakic eye using a mathematical definition, described at least by a geometry of a surface or surfaces that define a cornea, an axial position of a retina and an axial position of a plane where the intraocular lens will be situated after implantation,
    b) model a pseudophakic eye using a mathematical definition, described by an aphakic eye model in which a model of a defined lens is implanted where a combination of variable descriptive parameters within a combination of boundary conditions determine a geometry and characteristics of said model lens,
    c) define a merit function multiconfiguration which describes an optical quality of said pseudophakic eye model, said function integrating multiple configurations, each one corresponding to a distance to an object plane, associating a weight to each of said configurations to produce, as a result, a single value that represents a quality of the image of an evaluated system at different distances to an object plane,
    d) optimise said combination of variable descriptive parameters which define said model lens to determine a combination of descriptive parameters which produces an optimal result of said merit function multiconfiguration, and
    e) manufacture the refractive multifocal intraocular lens according to claim 1.

8. Method to manufacture a refractive multifocal intraocular lens according to claim 7, wherein said mathematical definition of an aphakic eye model of a) uses descriptive parameters which are representative of a particular population.

9. Method to manufacture a refractive multifocal intraocular lens according to claim 7, wherein said mathematical definition of an aphakic eye model of a) uses specific biometric parameters of a determined patient.

10. Method to manufacture a refractive multifocal intraocular lens according to claim 7, wherein a front and a back surfaces of the model lens of step b) are aspheric, have an elevation map with rotational symmetry with respect to an optical axis of said model lens and a progressive evolution along an entire topography.

11. Method to manufacture a refractive multifocal intraocular lens according to claim 7, wherein said distances to the object plane in step c) are distances between infinity and 0.4 m.

12. Method to manufacture a refractive multifocal intraocular lens according to claim 7, wherein said result of the merit function multiconfiguration of step c) is produced after tracing rays across a pseudophakic eye which includes the model lens, for each one of the configurations corresponding to each distance to the object.

13. Method to manufacture a refractive multifocal intraocular lens according to claim 7, wherein stage d) is carried out by an iterative process.

14. Method to manufacture a refractive multifocal intraocular lens according to claim 7, comprising the manufacture of a lens of a determined strength for distance vision and in that in step a) of the mathematical definition of the aphakic eye model, the axial length of the eye is that which provides a focused retinal image with a spherical monofocal lens of equal refractive strength.

15. Method to manufacture a refractive multifocal intraocular lens according to claim 14, wherein a nominal strength for distance vision of the refractive multifocal lens is attributed to that, a design of which is optimised in a range of focus for an eye with an axial length such that a monofocal lens with spherical surfaces, of the same material and the same thickness, with this same nominal strength, will generate a better image of an object situated 5 meters away from the retina.

16. Refractive multifocal intraocular lens produced by a method according to claim 7.

17. Refractive multifocal intraocular lens according to claim 1,
wherein said central region of intermediate optical strength presents a central local minimum optical strength, and is surrounded by a ring of global maximum optical strength with a smooth transition between them;
wherein the optical strength of any of said rings of varying strength is a local maximum optical strength or a local minimum optical strength, strictly smaller than said central local minimum optical strength;
wherein said rings of varying strength alternate smoothly.

18. Refractive multifocal intraocular lens according to claim 17, wherein said map of local optical strength is a smooth map.

* * * * *